US011457900B2

(12) United States Patent
Cerf et al.

(10) Patent No.: US 11,457,900 B2
(45) Date of Patent: Oct. 4, 2022

(54) MICRODEVICE FOR THE IN VIVO CAPTURE OF CIRCULATING CELLULAR BIOMARKERS

(71) Applicants: Centre National de la Recherche Scientifique, Paris (FR); Centre Hospitalier Universitaire de Toulouse, Toulouse (FR); Universite Toulouse III—Paul Sabatier, Toulouse (FR)

(72) Inventors: Aline Cerf, Toulouse (FR); Sylvain Sanson, Toulouse (FR); Hélène Cayron, Toulouse (FR); Alejandro Kayum Jimenez, Chiapas (MX); Christophe Vieu, Auzeville Tolosane (FR); Bernard Malavaud, Toulouse (FR)

(73) Assignees: Centre National de la Recherche Scientifique, Paris (FR); Centre Hospitalier Universitaire de Toulouse, Toulouse (FR); Universite Toulouse III—Paul Sabatier, Toulouse (FR)

( * ) Notice: Subject to any disclaimer, the term of this patent is extended or adjusted under 35 U.S.C. 154(b) by 0 days.

(21) Appl. No.: 15/547,203

(22) PCT Filed: Feb. 2, 2016

(86) PCT No.: PCT/FR2016/050218
§ 371 (c)(1),
(2) Date: Jul. 28, 2017

(87) PCT Pub. No.: WO2016/124854
PCT Pub. Date: Aug. 11, 2016

(65) Prior Publication Data
US 2018/0049726 A1 Feb. 22, 2018

(30) Foreign Application Priority Data
Feb. 2, 2015 (FR) ...................................... 1550806

(51) Int. Cl.
*A61B 10/02* (2006.01)
*A61F 2/01* (2006.01)
*A61F 2/06* (2013.01)

(52) U.S. Cl.
CPC ................ *A61B 10/02* (2013.01); *A61F 2/01* (2013.01); *A61F 2/06* (2013.01)

(58) Field of Classification Search
CPC ........ A61F 2002/018; A61F 2230/0006; A61F 2230/0069; A61F 2/01; A61F 2/90; A61B 5/6882; A61B 10/02
See application file for complete search history.

(56) References Cited

U.S. PATENT DOCUMENTS

| 4,685,472 A | 8/1987 | Muto | |
|---|---|---|---|
| 2002/0161394 A1* | 10/2002 | Macoviak | ........ A61B 17/12172 606/200 |

(Continued)

FOREIGN PATENT DOCUMENTS

| CN | 1278713 A | 1/2001 |
|---|---|---|
| CN | 103026228 A | 4/2013 |

(Continued)

OTHER PUBLICATIONS

International Search Report issued in corresponding International Application No. PCT/FR2016/050218 dated May 6, 2016.

(Continued)

*Primary Examiner* — Christian Jang
*Assistant Examiner* — Karen E Toth
(74) *Attorney, Agent, or Firm* — Morgan, Lewis & Bockius LLP

(57) ABSTRACT

The invention relates to a device for capture of cellular biomarkers circulating in an animal or human biological flow, characterised in that it is suitable for use in vivo and in that it comprises a means of filtration intended to retain (Continued)

Figure 6A:
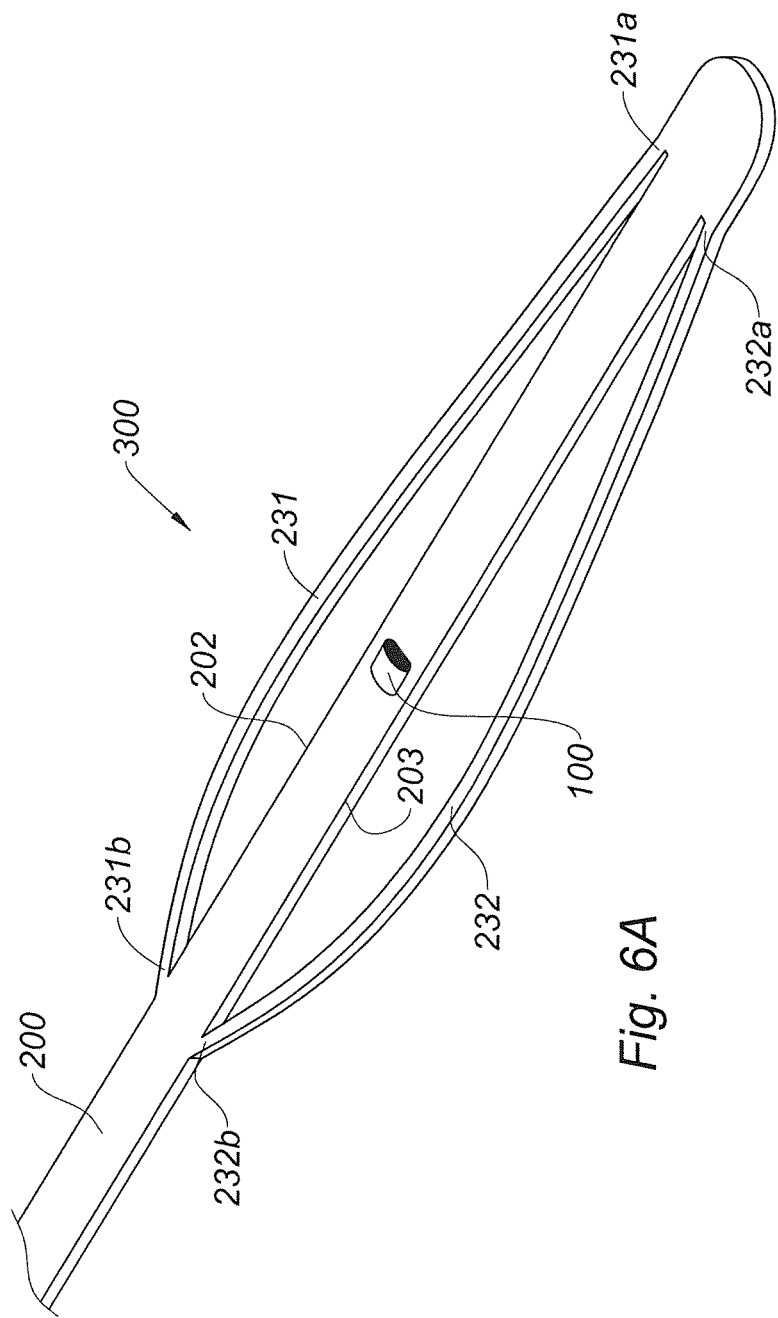

the said cellular biomarkers, the said means of filtration comprising at least one through-aperture the dimensions of which are suitable for retaining the said cellular biomarkers and being integral with a support, the support taking the form of a hollow component.

28 Claims, 6 Drawing Sheets

(56) References Cited

U.S. PATENT DOCUMENTS

| | | | | |
|---|---|---|---|---|
| 2003/0009189 | A1* | 1/2003 | Gilson | A61F 2/01 606/200 |
| 2004/0153118 | A1* | 8/2004 | Clubb | A61F 2/013 606/200 |
| 2004/0199201 | A1* | 10/2004 | Kellett | A61B 17/221 606/200 |
| 2005/0004597 | A1* | 1/2005 | McGuckin | A61F 2/013 606/200 |
| 2005/0153379 | A1* | 7/2005 | Hoon | A61B 5/6865 435/7.92 |
| 2005/0260355 | A1* | 11/2005 | Weber | A61L 27/303 427/566 |
| 2007/0207186 | A1* | 9/2007 | Scanlon | A61F 2/07 424/424 |
| 2011/0111412 | A1* | 5/2011 | Tai | B01D 61/18 435/6.14 |
| 2011/0244443 | A1 | 10/2011 | van Rijn et al. | |
| 2013/0202721 | A1* | 8/2013 | Silver | A61B 5/0031 424/718 |
| 2013/0296738 | A1* | 11/2013 | Swain | A61B 10/02 600/569 |
| 2014/0066729 | A1 | 3/2014 | Cosnier et al. | |
| 2014/0193833 | A1* | 7/2014 | Srivastava | G01N 33/57434 435/7.4 |
| 2015/0017638 | A1* | 1/2015 | Rhim | G01N 33/5011 435/6.11 |

FOREIGN PATENT DOCUMENTS

| | | |
|---|---|---|
| EP | 2523605 A1 | 11/2012 |
| WO | 99/16382 A2 | 4/1999 |
| WO | 99/23976 A1 | 5/1999 |
| WO | 9923976 A1 | 5/1999 |
| WO | 9932976 A1 | 5/1999 |
| WO | 2004/06089 A1 | 1/2004 |
| WO | 2007/093009 A1 | 8/2007 |
| WO | 2011/123655 A1 | 10/2011 |
| WO | 2013/025531 A1 | 2/2013 |

OTHER PUBLICATIONS

Office Action with Search Report issued in corresponding Chinese Patent Application No. 201680007640.2 dated Jul. 7, 2020.

* cited by examiner

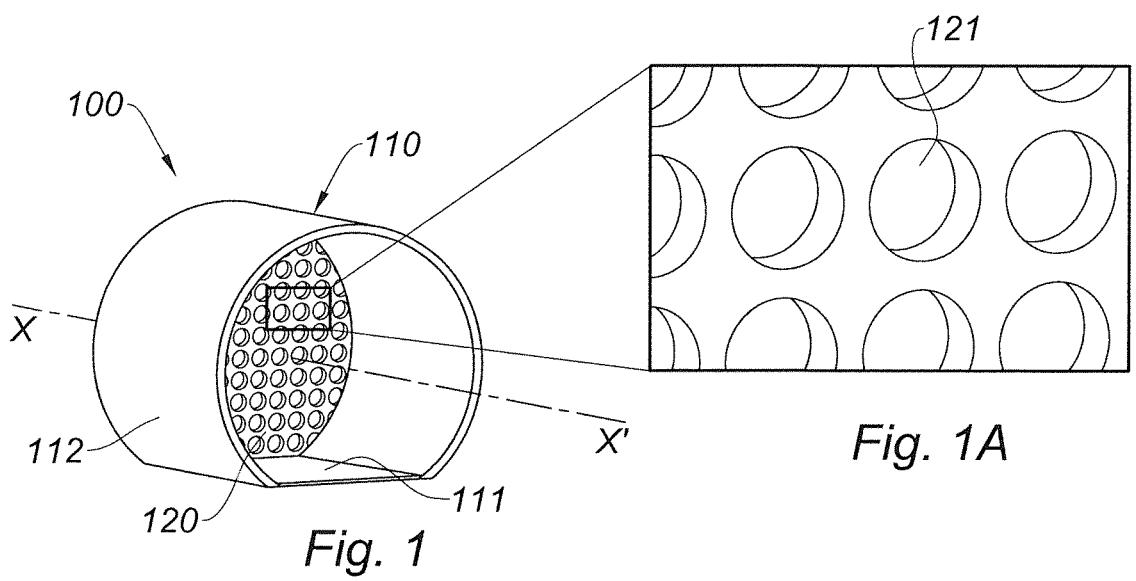
Fig. 1
Fig. 1A
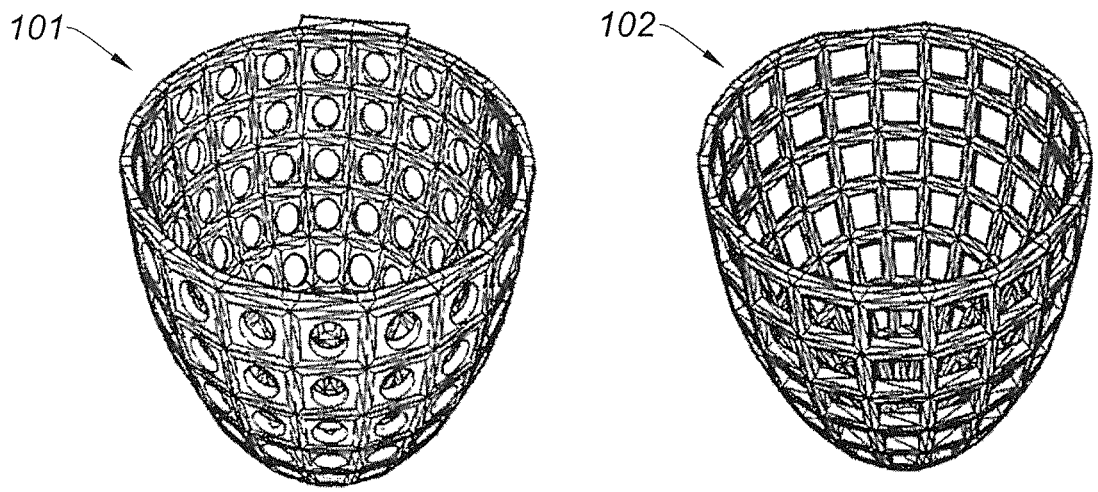
Fig. 2A
Fig. 2B
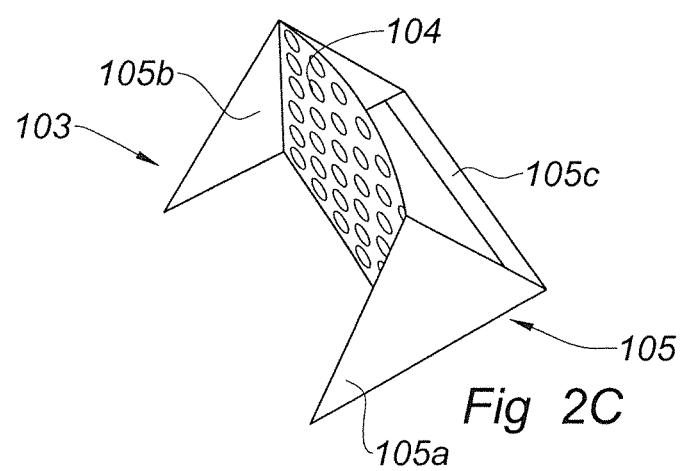
Fig 2C

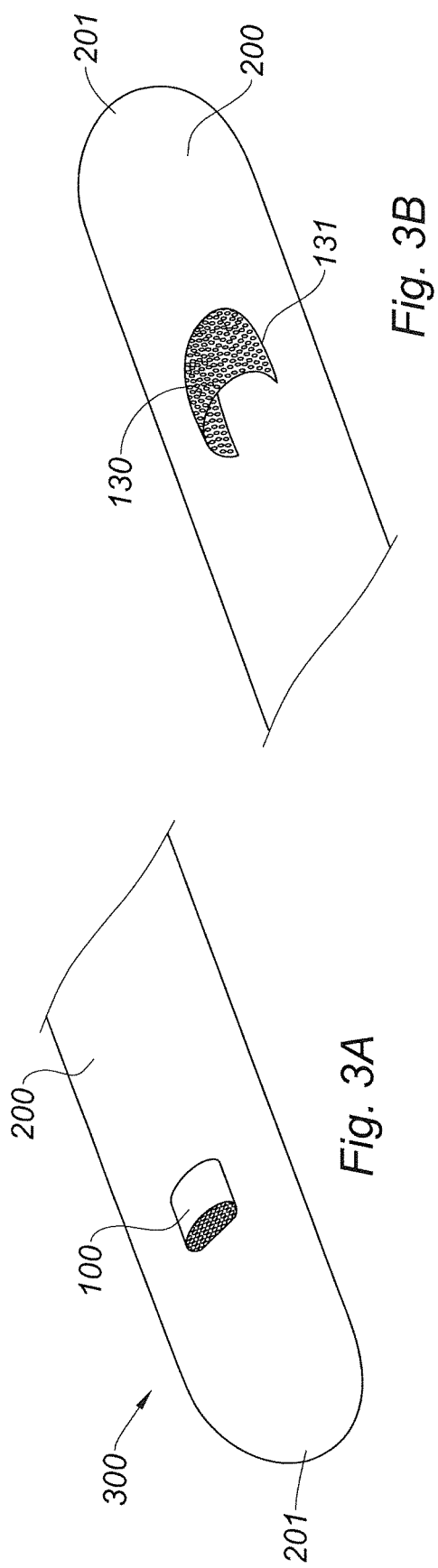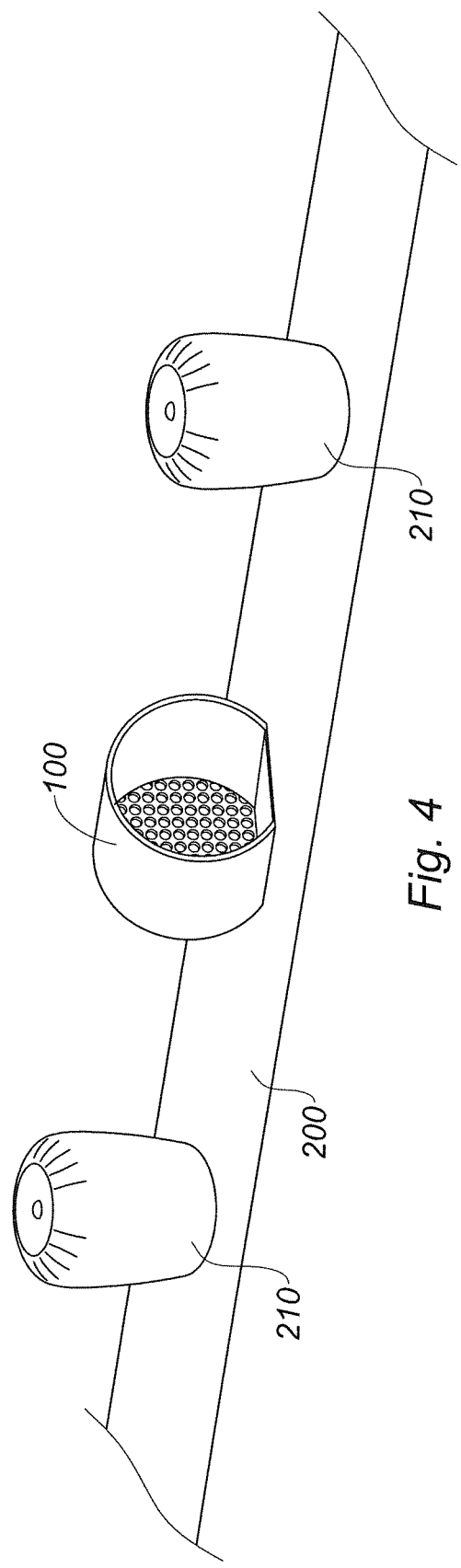

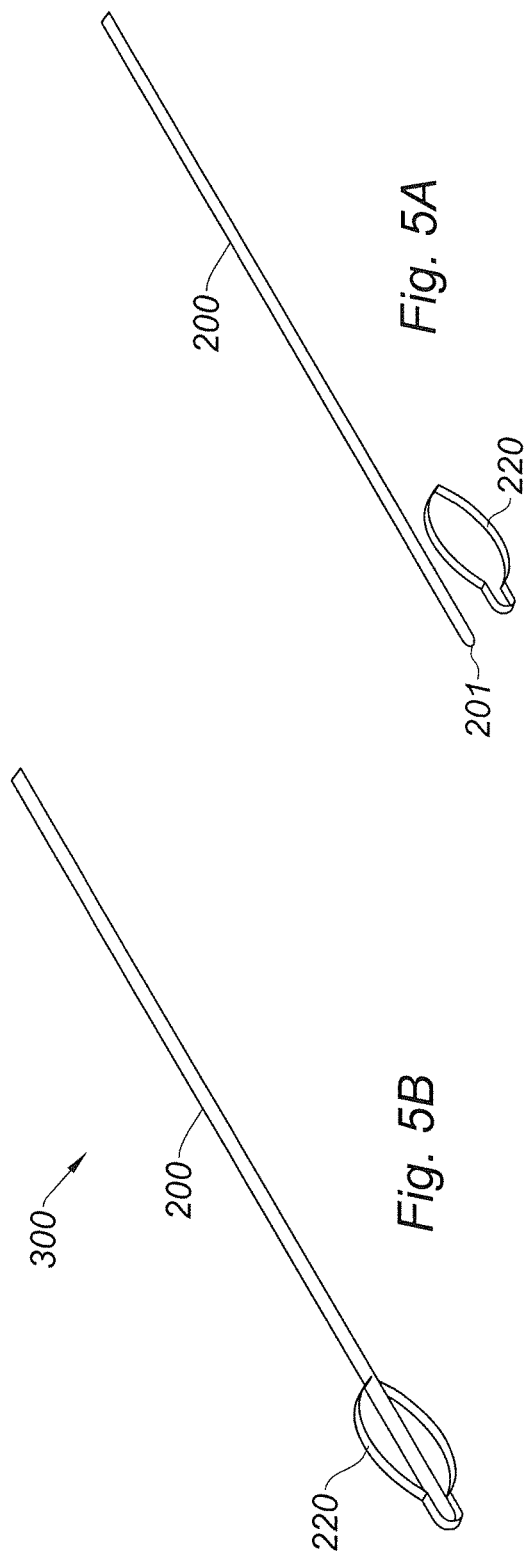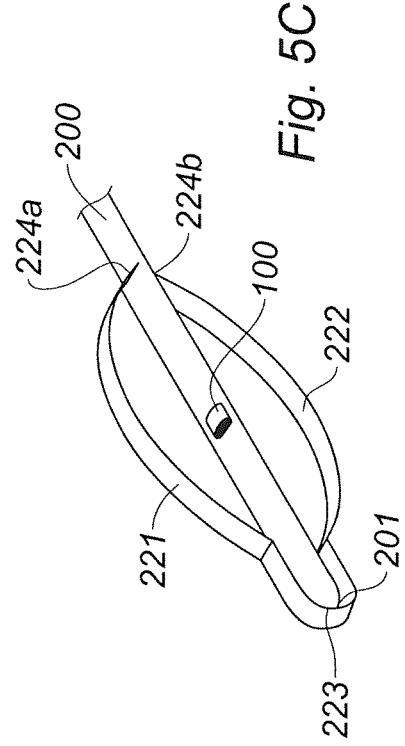

MICRODEVICE FOR THE IN VIVO CAPTURE OF CIRCULATING CELLULAR BIOMARKERS

The invention lies in the field of devices for capture and sampling of cells of interest present in the circulation of a biological flow such as the blood and the analysis of which after capture inter alia makes it possible to make a diagnosis.

For some years, the trend in the identification and treatment of cancers has been towards the personalisation of care, which is implemented through the fine study of the tumour cells. These cells are usually sampled by biopsy. However, a biopsy is invasive, and alternative methods have been developed in order to avoid it.

Cancerous tumours release cells referred to as "circulating tumour cells" or CTCs into the blood circulation; it is commonly accepted that this phenomenon appears at an early stage of the disease. Immunohistochemical analysis of these cells makes it possible to make a diagnosis and to provide information in particular on the aggressiveness of the cancer. The CTCs thus represent a biomarker of interest at all times in the care of cancer disease, diagnosis, prognosis and monitoring.

Now, the CTCs are present in extremely low concentration in the blood of patients suffering from cancer (about $1/10^9$ normal blood cells) (Nagrath, S., et al.). The isolation of these cells is thus extremely difficult. Various procedures are known for effecting this isolation.

The CellSearch® system is based on immunodetection. It is based on the presence of EpCAM, a membrane antigen specific to cells of epithelial origin, on the surface of the CTCs. A sample of 7.5 ml of blood is centrifuged, then contacted with ferromagnetic nanoparticles provided with anti-EpCAM antibodies on their surface. The CTCs are then separated from the other cells by application of a magnetic field. This system has a double disadvantage:
  it utilises a very limited sample of blood (7.5 ml, which corresponds to 0.15% of the total blood volume), in which the number of CTCs, owing to their low concentration, is very low,
  it does not make it possible to detect CTCs which have lost the protein EpCAM during the epithelial mesenchymal transition (EMT) (Small, A. C., et al.) which represents about ⅔ of the total population of these cells; moreover, it only allows the detection of differentiated cells whose lifetime is limited and which are not the most dangerous.

Other approaches are known for isolating CTCs in vitro from a blood sample, based on the size of the CTCs. In particular the ISET system ("Isolation by Size of Epithelial Tumour Cells") utilises the filtration of a sample of treated blood (prior lysis of the red cells) on a micro-perforated polycarbonate membrane; in this system, the CTCs are previously rigidified by application of paraformaldehyde so as to resist the strong pressure which is applied (Williams, A., et al.).

In general, the sensitivity of the in vitro detection is reduced owing to the low volume of the samples. In fact, given the rarity of the CTCs in the blood, their presence in a sample of a few millilitres can amount to a few units at an already advanced stage of the cancer. Their detection at much earlier stages is in fact almost impossible.

From WO 2010/145 824, the GILUPI® system, which enables in vivo detection, is known. This system is based on the functionalisation of a metal rod by means of anti-EpCAM antibody introduced into the blood circulation. This system makes it possible to avoid the limitation inherent in the low volume of the samples, but it remains limited by the immunological method of capture.

The purpose of the invention is to propose a device which makes it possible to avoid the disadvantages connected with sampling and with immunological methods for isolating circulating cellular biomarkers. For this purpose it proposes a device for capture of cellular biomarkers circulating in an animal or human biological flow, characterised in that it is suitable for use in vivo and in that it comprises a means of filtration intended to retain the said cellular biomarkers, the said means of filtration comprising at least one through-aperture the dimensions of which are suitable for retaining the said cellular biomarkers and being integral with a support, the support taking the form of a hollow component.

The device according to the invention is based on the physical properties of the circulating cellular biomarkers, size and deformability. Platelets have a size of 2 to 4 μm and red cells a size of about 7 μm; white cells have variable dimensions, from 7 to 25 μm, but they are very deformable, which enables them to circulate in the smallest blood vessels. Among the circulating cellular biomarkers, the circulating tumour cells, in particular, have variable dimensions, lying between 4 and 25 μm, but they are very poorly deformable. Consequently, it is possible to provide a means of filtration which retains the circulating cellular biomarkers such as the CTCs while allowing all the other components of the biological flow to pass through under in vivo conditions, in particular of pressure and speed. The capture device according to the invention only utilises the physical properties (size, deformability) of the cellular biomarkers; thus any hypothesis concerning the presence of membrane proteins on the surface of the CTCs is avoided. Preferably, the device does not comprise means for capture of cellular biomarkers based on chemical affinities of the biomarkers. The cellular biomarkers penetrate into the hollow of the support, and owing to their physical properties are retained by filtration. This form of the capture device makes it possible to limit the phenomenon of recirculation of the cellular biomarkers. On the one hand, the capture device having a hollow support, it makes it possible to avoid the biomarkers escaping laterally. Moreover, the capture device also makes it possible to avoid biomarkers having penetrated into the capture device being entrained to the outside of the latter by movements of the flow within it. The capture device is in particular intended to limit contra-rotating vortices.

Examples of biological flows are the blood, lymph, urine . . . .

Examples of circulating cellular biomarkers for which the capture device is suitable are the stromal and epithelial cells, circulating foetal cells (CFC), stem cells, clusters or aggregates of tumour cells, tumour cells associated with all types of cancer: prostate tumour cells, breast or colon cancer cells, . . . and the other cell types: monocytes (macrophages). The device according to the invention is thus particularly suitable for the diagnosis of different types of cancers through the capture of circulating tumour cells, in particular.

Cellular biomarkers are also understood to mean infesting elements of large size such as intra or extracellular parasites or their eggs. For example, leishmaniosis can be diagnosed by the presence of its infective, promastigote form, with a size of 10 μm to 15 μm. Similarly, schistosomiasis can be diagnosed by the presence of its eggs with a size of 70 μm to 200 μm.

Preferably, the cellular biomarkers are eukaryotic cells. These cells can be single or in the form of aggregates.

The diagnosis of other diseases could be envisaged following the capture of other circulating cellular biomarkers capable in particular of exhibiting abnormalities. The diagnosis of physiological conditions other than diseases or the prevention of diseases can also be envisaged through the capture of circulating cellular biomarkers.

The capture device according to the invention is suitable for use in vivo. In particular, it can be provided for being placed in the flow of the blood circulation. The means of filtration is thus associated with a support to rigidify it and/or to retain it within the biological flow and enable its recovery. The capture device can be an in vivo, in vitro or ex vivo capture device. Preferably, the capture device is an in vivo device. However, the possibility that it could be utilised ex vivo or in vitro is not excluded.

The capture device can comprise one or the other of the following characteristics, alone or in combination.

Advantageously, the capture device is capable of filtering cellular biomarkers when the biological flow pressure to which it is subjected lies between 9 and 16 mm Hg. These pressures are typically the pressures which are found in biological flows in vivo, in the peripheral veins (Munis, J. R. et al.).

Advantageously, the means of filtration can comprise at least one through-aperture, the dimensions of which are suitable for retaining the cellular biomarkers on the basis of their size and their deformability in the bloodstream.

The dimensions are for example the depth and at least one transverse dimension.

Advantageously, at least one aperture can be substantially circular or substantially oval or substantially polygonal, or take the form of a crack.

The invention is not limited by the shape of the apertures, provided of course that they are through-apertures. The shape and the size of the apertures can vary within the thickness of the means of filtration in order to allow the capture of different types of cellular biomarkers with different thicknesses. The wall of these apertures can form a truncated cone, but preferably it forms a cylinder, that is to say comprising parallel generatrices.

The means of filtration can comprise only one aperture, for example in the form of a crack, rectilinear or curved, the minimum dimension of which is selected to be able to retain the cellular biomarkers under consideration or several apertures, equally or unequally distributed over the means of filtration, of the same shape and dimension or of different shape and/or dimensions.

According to a preferred embodiment, each aperture exhibits a transverse dimension, preferably its minimum transverse dimension, lying between 1 µm and 200 µm, more preferably between 1 µm and 100 µm, still more preferably between 5 µm and 100 µm. In particular, each aperture exhibits a transverse dimension preferably lying between 1 µm and 25 µm for cellular biomarkers of the CTC type, more preferably between 5 µm and 25 µm, still more preferably between 12 µm and 25 µm, the optimum diameter in this case being in the vicinity of 12 µm.

Preferably, each through-aperture of the means of filtration is circular. The transverse dimension then corresponds to the diameter of the aperture.

According to a preferred embodiment, the support is a hollow component open at one end and closed at another end by the means of filtration. Preferably, the support extends along a longitudinal direction. The aperture of the support can then be at one longitudinal extremity and the means of filtration at the opposite longitudinal extremity.

Advantageously, the means of filtration can be planar.

The invention is not limited by the shape of the means of filtration either, but it is preferably planar.

According to one embodiment, the support possesses a rotational symmetry about an axis. The support can have a total rotational symmetry about an axis or have a partial rotational symmetry and be truncated along a plane parallel to the axis. By utilising a device with a rotational symmetry, the perturbation of the course of the biological flow is diminished when the device is placed with its axis of revolution in the principal direction of the biological flow. This type of shape in particular makes it possible to diminish the risk of thrombosis when the device is utilised in vivo. The truncated part makes it possible to better attach the capture device onto a means of introduction. It is preferably intended to be in contact with the means of introduction. The axis of revolution is preferably the longitudinal direction along which the support extends.

The capture device can for example take the form of a cylinder, or a truncated or non-truncated cone or paraboloid.

The means of filtration can form all or a part of the bottom of the support. Preferably, the means of filtration forms the bottom of the support.

Advantageously the device can have a rotational symmetry about an axis. The capture device can for example take the form of a cylinder or of a cone, or of a cylinder surmounted by a cone or by a spherical cap.

In a preferred embodiment, the device can take the form of a hollow cylinder, truncated along a plane parallel to the axis of the cylinder, and the means of filtration can form the bottom of the truncated cylinder.

The support can contain at least one substantially circular or substantially oval or substantially polygonal through-aperture or takes the form of a crack. Preferably, the support does not contain a through-aperture the dimensions of which are intended for retaining the cellular biomarkers.

The invention is not limited either by the presence or absence of through-apertures in the support, their shape or their number, which can be different from those of the apertures present on the means of filtration.

According to one embodiment, the support and the means of filtration form a single part.

Advantageously, the device, means of filtration and support can be made of a photosensitive resin.

The device, means of filtration and support, can be made by three dimensional laser lithography or conventional photolithography: the resin is polymerised at the site where it is irradiated, then the non-polymerised resin is dissolved.

Advantageously, the device can be made of a biocompatible material or it can be covered with a biocompatible material, for example a polymer such as parylene, or it can be covered with a biocompatible metallic layer (Au, Ti, . . . ). This biocompatible material can also take the form of a gel compatible with the cell culture.

Advantageously, the capture device can be functionalised by means of an anti-thrombotic compound such as heparin so as to avoid the risk of thrombosis or coagulation. The device can in particular be exposed to various surface treatments aiming to modify its adsorption properties towards circulating biological entities. These treatments can be plasma treatments enabling either control of the surface tension, the surface chemical reactivity or the surface roughness but also chemical treatments of grafting or functionalisation. Advantageously, the capture device can be functionalised by means of an anti-thrombotic compound.

The invention also relates to a device for sampling cellular biomarkers, comprising at least one capture device for biomarkers according to the invention attached onto a means of introduction of the capture device into a biological flow vessel.

It is advantageous that the capture device be associated with a means of introduction in order to introduce it easily into a biological flow vessel, in particular a blood vessel, an artery or preferably a vein, or a lymph vessel. The capture device can be attached directly to the means of introduction or via a part such as a stud. Of course, the sampling device can comprise several capture devices, which can be different from one another, in particular as regards the shape and the diameter of the apertures.

In one modification, the means of introduction of the capture device into the blood circulation can form the support.

In this modification, there is identity between the support of the means of filtration and the means of introduction.

Advantageously, the means of introduction of the capture device into the blood circulation can comprise a strip.

A fine strip, for example metallic, can be used as a means of introduction of the capture device into the blood vessel.

Advantageously, the strip can comprise a metal alloy or a composite material based on resin and fibres.

It can be a stainless steel or an alloy of nickel and titanium such as Nitinol, known for its biocompatibility properties and its flexibility. Indeed, the strip must be of a material sufficiently flexible to be capable of insertion along the longitudinal axis of the blood vessel.

In the case of a strip of stainless steel or composite material, this can be covered with a biocompatible material such as parylene or a biocompatible metallic layer (Au, Ti, . . . ). The deposition of biocompatible material also makes it possible to impart rigidity to the strip or to improve its mechanical behaviour.

Advantageously, the means of introduction can comprise a first means of protection of the means of filtration intended to avoid detachment of the means of filtration.

It is advantageous to protect the means of filtration of the capture device, or indeed the capture device as a whole, in order to avoid its detachment from the means of introduction during the introduction or withdrawal manoeuvre. For this purpose, the sampling device can contain a first means of protection. One function of this first means of protection can also equally be to centre the sampling device relative to the flow in the blood vessel, and also relative to the catheter when it is introduced in a catheter.

Advantageously, the first means of protection can comprise at least one stud attached to the means of introduction.

The means of introduction can for example comprise two studs flanking the capture devices or devices and sufficiently far away not to perturb the blood flow.

Advantageously, the means of introduction can comprise a second means of protection intended to protect a blood vessel into which it is brought to be introduced.

It is advantageous to protect the walls of the blood vessel from the foreign body that the sampling device represents.

Advantageously, the sampling device can contain an end part attached to the extremity of the means of introduction and forming a first and/or a second means of protection.

Advantageously, the end part can comprise at least one arch.

An arch is understood to mean an elongated curved part comprising a first and a second extremity, which can be joined to the strip by at least one of its extremities.

When the end part is attached to the extremity of the sampling device, the at least one arch presses non-aggressively on the wall of the vessel and centres the device in the interior of the vessel and of the catheter when a catheter is utilised. The at least one arch can also be intended to protect the capture device.

In another modification, the means of introduction can contain in the vicinity of its extremity at least one longitudinal arch forming a first and/or a second means of protection.

Advantageously, the sampling device can be covered with biocompatible material such as parylene.

Advantageously, the sampling device can be functionalised by means of an anti-thrombotic compound, for example heparin.

Advantageously, the sampling device can contain a gripping means so as to make it suitable for use in a catheter.

The sampling device can comprise a "stopper", that is to say gripping means such as a plastic stopper placed on the distal extremity of the means of introduction, facilitating the gripping of the device and serving as a stop during the introduction of the device into the catheter. The extremity which is opposite that which contains the capture device is called the distal extremity of the sampling device.

Advantageously, the sampling device can be inserted in a catheter.

The invention also relates to a set for sampling cellular biomarkers comprising a catheter and a sampling device according to the invention, said device being inserted in the catheter.

A perfusion catheter, possibly functionalised by means of an anti-thrombotic compound such as heparin, guides and advantageously protects the sampling device. The catheter is introduced into the blood vessel, the sampling device is inserted into the interior of the catheter, and then the sampling device is pushed out of the catheter to be placed in the blood flow. At the end of the sampling, the reverse manoeuvre is performed: reinsertion of the sampling device into the catheter, and withdrawal of the catheter. The captured cells can then be either counted, immunologically labelled and put into culture directly on the capture device, or easily recovered for counting, immunolabelling and return to culture in vitro.

The advantages of the device according to the invention are as follows:
 It is suitable for use in vivo. Typically, its dimensions allow its introduction into a biological channel such as a blood vessel.
 It only utilises the physical properties (size and deformability) of the cellular biomarkers, hence there is no need to be concerned with the real or supposed presence of specific membrane proteins on the surface of the cellular biomarkers,
 The blood circulation can be utilised directly as a fluidic system,
 The volume of blood analysed is considerably greater; the device can analyse 100 ml of blood in 5 minutes, that is to say a volume 10 to 100 times greater than that analysed by the systems which utilise a sample,
 The number of captures can be increased by increasing the sampling time and by providing a device comprising several capture devices,
 It is applicable to any type of circulating cellular biomarker mentioned above by adapting its geometry, in particular the size of the apertures.

The invention also relates to a method for detecting a disease or a physiological condition in a patient including a stage of capture of a cellular biomarker by the capture device according to the invention and a stage of analysis of the captured cellular biomarkers.

The stage of capture of the cellular biomarker can be performed in vivo, in vitro or ex vivo.

The analysis stage can be a quantitative or qualitative analysis stage. For example, a determination stage can be a stage for determining if the cellular biomarkers are cancerous cells.

The analysis stage can include a stage of returning the cellular biomarkers to culture.

The invention relates to a device for capture of cellular biomarkers according to the invention for use for diagnostic purposes, in particular for the purposes of cancer diagnosis.

The invention also relates to a method for detecting a disease or a physiological condition in a patient including a stage of capture of a cellular biomarker by the sampling device according to the invention and a stage of analysis of the cellular biomarkers captured.

The invention also relates to a device for sampling cellular biomarkers according to the invention for use for diagnostic purposes, in particular for the purposes of cancer diagnosis.

The invention also relates to a method for detecting a disease or a physiological condition in a patient including a stage of capture of a cellular biomarker by the sampling set according to the invention and a stage of analysis of the cellular biomarkers captured.

The invention also relates to a set for sampling cellular biomarkers according to the invention for use for diagnostic purposes, in particular for the purposes of cancer diagnosis.

The invention also relates to a method for treating a disease in a patient including a stage of capture of a cellular biomarker by the capture device according to the invention.

The invention relates to a device for capture of cellular biomarkers according to the invention for use for therapeutic purposes, in particular for the purposes of cancer therapy.

The invention also relates to a method for treating a disease in a patient including a stage of capture of a cellular biomarker by the sampling device according to the invention.

The invention also relates to a device for sampling cellular biomarkers according to the invention for use for therapeutic purposes, in particular for the purposes of cancer therapy.

The invention also relates to a method for treating a disease in a patient including a stage of capture of a cellular biomarker by the sampling set according to the invention.

The invention also relates to a set for sampling cellular biomarkers according to the invention for use for therapeutic purposes, in particular for the purposes of cancer therapy.

Figure 6B:
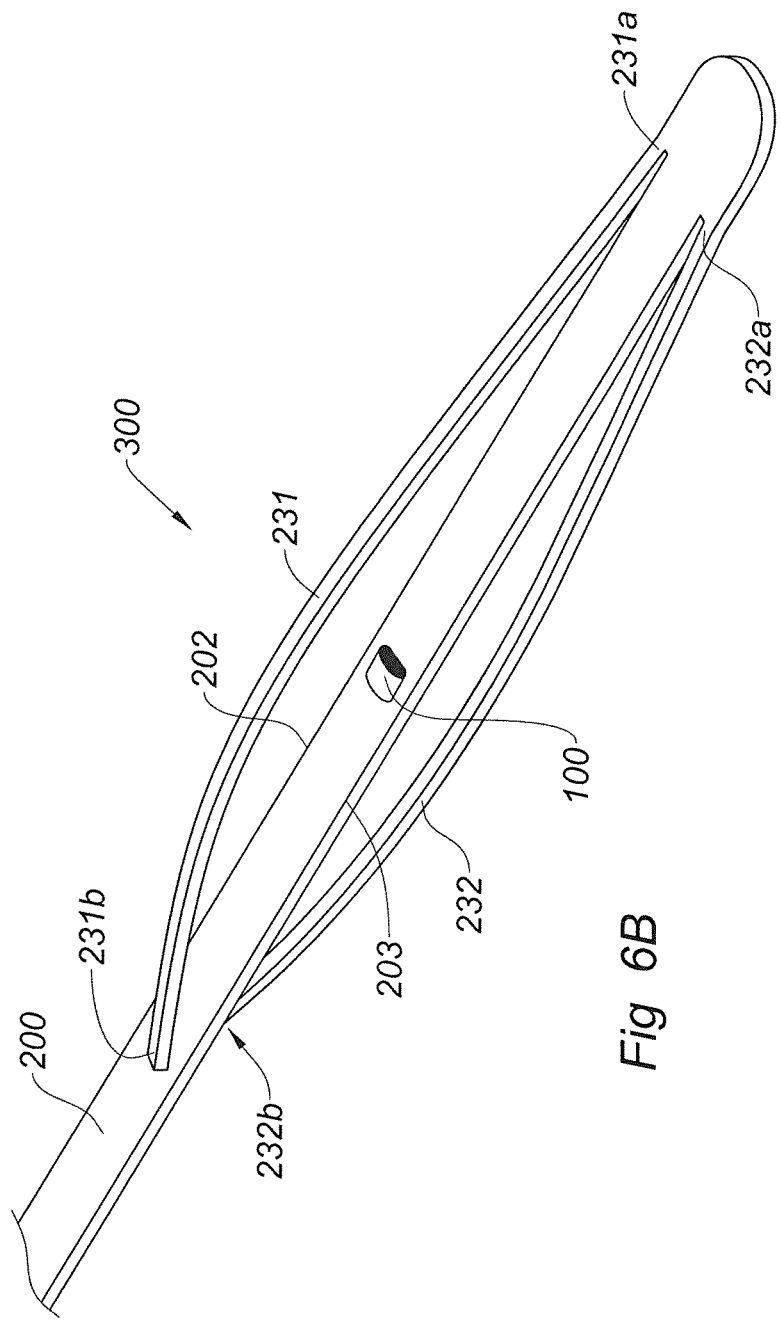

Embodiments and modifications will be described below, as non-limiting examples, with reference to the appended drawings in which:

FIG. 1 shows a perspective view of a capture device, FIG. 1A being an enlarged view of a part of this device, FIGS. 2A and 2B show perspective views of modifications of the means of filtration, and FIG. 2C shows a perspective view of one capture device modification, FIGS. 3A and 3B show the extremities of two embodiments of a sampling device, FIG. 4 shows the extremity of a sampling device containing two means of protection, FIGS. 5A and 5B show the extremity of a sampling device and an end protection part, and FIG. 5C is an enlarged view of FIG. 5B, FIGS. 6A and 6B show the extremity of a sampling device containing a protection and centring means in two modifications, FIGS. 7A to 7E show capture device modifications.

The capture device 100 illustrated in FIG. 1 comprises a cylindrical support 110 truncated along a plane parallel to the axis X-X' of the cylinder, i.e. this support comprises a flat part 111 and a round part 112. As will be seen later, the flat part 111 is useful for the attachment of the device onto a means of introduction; however, the device could be attached by a generatrix of a non-truncated cylinder or on the edges of the generatrix of the truncated cylinder.

At a first extremity, the cylinder is closed by a flat bottom 120 and it is open at its other extremity. The bottom 120 constitutes the means of filtration of the device 100 in the form of a filter membrane. As is visible in FIG. 1A, the filter membrane 120 comprises a series of through-apertures 121 of cylindrical shape of circular section of the same diameter.

The capture device 100 is intended to be placed in the blood circulation, the aperture facing upstream in the circulation in such a manner that the biomarkers sought penetrate into the capture device and are retained by the filter 120. It is important that these biomarkers do not escape from the capture device once they have entered it. Now in certain configurations, digital simulations have shown that recirculation vortices could exist in the interior of the device and that the biomarkers could escape from these. In the case of the cylindrical device illustrated in FIG. 1, this phenomenon occurs when the support 110 contains the same apertures 121 as the filter 120. In the preferred embodiment illustrated in FIG. 1, the round part 112 of the support does not contain any aperture and makes it possible to maintain an essentially laminar flow during the passage of the blood flow through the device.

FIGS. 2A, 2B and 2C illustrate other embodiments of the capture device. In FIGS. 2A and 2B, the devices 101, 102 contain a means of filtration which takes the form of a paraboloid of revolution, the support of the means of filtration in this case being constituted of a means of introduction such as a strip. The device 101 contains circular apertures, and the device 102 contains polygonal apertures. These devices can be truncated or provided with a base or pedestal to facilitate their attachment onto a means of introduction as previously mentioned with reference to FIG. 1.

FIG. 2C illustrates a capture device 103 comprising a flat filter 104 firmly held by a support 105 comprising two uprights 105a and 105b linked by a crossbar 105c parallel to the plane of the filter 104.

The dimensions of the device are suitable for its implementation in a blood vessel; in order not to create a risk of thrombosis in particular, it must not perturb the blood circulation.

In the case of the device 100 illustrated in FIG. 1, the dimensions are as follows:

Diameter lying between 50 µm and 3 mm, preferably between 50 µm and 1.7 mm, more preferably close to 200 µm, according to one embodiment, the diameter of the device lies between 0.5% and 15% of the diameter of the channel into which the device is introduced, preferably between 0.5% and 5% in particular in the case where the capture device is destined to be placed in the basilic vein, Length lying between 50 µm and 3 mm, preferably close to 150 µm, preferably greater than the sum of the thickness of the wall of the device and the diameter of the cellular biomarker destined to be captured, Diameter of the apertures lying between 1 µm and 200 µm, preferably between 1 µm and 100 µm, still more preferably between 5 µm and 100 µm in general for the cellular biomarkers mentioned above and between 1 µm and 25 µm, more preferably between 5 µm and 25 µm, still more preferably between 12 µm and 25 µm for the CTCs; surprisingly, and as a non-limiting example, it has been found that for tumour cells of PC3 prostatic lines of size lying between 12 μm and 25 μm, the capture device was very sensitive to the diameter of the apertures, the optimum diameter in this case being close to 12 μm;

When the aperture takes the form of a crack, its transverse dimension lies between 1 μm and 200 μm, preferably between 1 μm and 100 μm, still more preferably between 5 μm and 100 μm, preferably lying between 1 μm and 25 μm, more preferably between 5 μm and 25 μm, still more preferably between 12 μm and 25 μm, and preferably close to 12 μm, The apertures can be of truncated cone shape, the diameter varying from 1 μm and 200 μm, preferably from 1 μm and 100 μm, still more preferably from 5 μm and 100 μm approximately for the cellular biomarkers, preferably between 1 μm and 25 μm, more preferably between 5 μm and 25 μm, still more preferably between 12 μm and 25 μm, from about 15 μm to about 8 μm for the CTCs, in such a manner as to retain the cellular biomarkers and more particularly the CTCs in the interior of the apertures, Thickness of the wall of the support and of the filter membrane lying between 5 μm and 20 μm, preferably close to 9 μm; preferably the thickness of the filter membrane is close to 6 μm and that of the wall close to 10 μm to improve the mechanical behaviour of the capture device, In the case of a flat and rectangular filter membrane plane such as is illustrated in FIG. 2C, characteristic dimensions of the uprights will lie between 50 μm and 1.5 mm.

The capture device can be made from a photosensitive resin processed by three-dimensional laser lithography or any other lithography technique suitable for the dimensions of the device.

As regards biocompatibility, the invention proposes two options:

Either the resin utilised is biocompatible,

Or the device once made is covered with a biocompatibility film such as parylene or in a biocompatible metal such as Au, Ti . . . .

The capture device of the invention is not limited by the preceding description. In particular:

The plane of truncation could be angularly shifted relative to the axis X-X',

The support could have a shape other than cylindrical, for example conical, spherical, truncated or not truncated by a plane, When the support does not possess an axis of revolution, the shape of the support is not limited to the use of two uprights and one crossbar, The filter membrane could also be placed along a section of the cylinder and not constitute its bottom, that is to say that the support 110 could contain a downstream part of the bloodstream, The bottom 120 of the cylinder, forming the filter membrane of the device 100, could be non-planar, but for example take the form of a hemispherical cap or a cone.

FIG. 3A illustrates a sampling device 300 comprising a capture device 100 attached onto a means of introduction, here a strip 200, by the flat part 111 of the support 110, in the vicinity of the extremity 201 of the strip. It can be attached by welding or metal deposition or utilisation of a biocompatible glue or resin.

The strip 200 is made of Nitinol, which is an alloy of nickel and titanium and which has the property of being biocompatible and flexible which makes it possible to facilitate its introduction into the blood vessel. In the case where it were constituted of another, non-biocompatible material, it would be covered, at one stage of its manufacture, with a film of biocompatible material such as parylene.

The width of the strip lies between 300 μm and 3 mm, preferably between 300 μm and 1.5 mm, preferably close to 900 μm, so as to be compatible with the internal diameter of the catheters in which the strip can be inserted. In the case of a strip of Nitinol, its thickness lies between 50 μm and 76 μm. When cut out, it is several centimetres in length, for example 5 cm, but the length effectively introduced into the blood circulation is limited to 1 cm or 2 cm.

FIG. 3B illustrates an embodiment in which the support of the membrane 130 is constituted of the strip 200. The filter membrane is attached onto the strip 200 by an edge 131 in such a manner as to exhibit an aperture intended to be oriented facing upstream in the blood flow. The filter membrane is configured in such a manner as not to perturb the blood flow.

A risk associated with the sampling device 300 is that the capture device or devices 100 detach from the strip 200 and enter the blood circulation, for example at the moment of introduction or withdrawal of the sampling device. For this reason, as illustrated in FIG. 4, the strip 200 comprises first means of protection in the form of studs 210 attached onto the strip 200 on both sides of one or several capture devices 100 in the longitudinal direction. The studs illustrated in FIG. 4 have the shape of a "barrel" with a round top, but they could have a cylindrical, hemispherical or truncated cone shape . . . provided that they take the form of a relatively massive body on the scale of the device and are of rounded shapes so as not to perturb the blood circulation nor injure the vessel wall.

The studs 210 are sufficiently close to the capture device 100 to provide it with protection but sufficiently far away, for example separated by about 1 mm, not to perturb the bloodstream around the capture device 100.

The studs 210 glued onto the strip can advantageously be constituted of resin and manufactured with the same manufacturing process as the capture device 100, without this being limiting.

Another advantage of the studs 210 is that they can participate in the function of centring the sampling device in the vessel and/or in a catheter.

Another risk associated with the sampling device 300, particularly in view of the capture time of several minutes, is that of damaging the wall of the vessel in which it is inserted. For this reason, the invention proposes two second means of protection:

FIGS. 5B and 5C show a strip 200 equipped with an end piece 220 intended to be attached onto the strip, in the vicinity of its extremity; this end part 220 forms two arches 221, 222 joined at a first common extremity 223, and the second extremities 224a, 224b of which are free; this end piece 220 is attached onto the strip 200 on the one hand joining the common extremity 223 and the extremity 201 of the strip, and on the other hand by attaching the second extremities 224a, 224b onto opposite faces of the strip; these arches 221, 222 press non-aggressively against the wall of the vessel and protect it; they also protect the capture device 100 attached onto the strip 200 between the first and second extremities of these arches from being torn off;

FIG. 6A shows a strip 200, a lamella 231, 232 of which is detached from each of the edges 202, 203 of the strip 200 and forms an arch, the extremities 231a, 231b, 232a, 232b of these lamellae remaining attached to the strip; the lamellae 231, 232 extend on both sides of the plane of the strip 200 such that, as in the case of FIG. 5, these arches protect the vessel and centre the sampling device 300 in the vessel. In the modification of FIG. 6B, only the downstream extremities 231a, 232a remain attached to the edges 202, 203 of the strip 200; the lamellae 231, 232 are lightly twisted such that the upstream extremities 231b, 232b have been detached from the edges of the strip 200 and are attached onto the plane of the strip and on both sides. Of course, the invention also relates to the symmetrical configuration, where only the upstream extremities 231b, 232b of the lamellae remain attached to the edges of the strip and where it is the downstream extremities which are attached onto the plane of the strip and on both sides.

The invention is not limited by the preceding description:
The means of introduction could possibly not be planar and take another shape, for example that of a cylinder or a wire,
The sampling device 300 could comprise several capture devices, for example aligned longitudinally or staggered, so as not to perturb the blood flow too much, or transversely on the strip 200, with the capture devices possibly being different two by two in particular in terms of shape, size, dimension and size of apertures.

EXAMPLES

Digital Simulation
Equipment and Methods:

In order to evaluate the impact of the capture device on the flow velocity, Reynolds number, shear stresses and platelet activation, the influence of various prototypes of capture device on the blood flow was simulated by "computational fluid dynamics" (CFD). This stage of digital simulation of the fluid-structure interaction (FSI) was performed by means of the Ansys Fluent® 15.0 software. A bibliographic study made it possible to define the constants governing the flow of the bloodstream, as well as the most appropriate calculation algorithms.

The blood is considered as a non-Newtonian fluid which signifies that its viscosity depends on the shear level, in contrast to Newtonian fluids, whose viscosity is constant. It is critical to take account of this property. Among the different models for simulating the viscosity of non-Newtonian fluids, the power law model was selected (Petkova, S., et al.). This model is written according to the following formula: $\eta_{min} > \eta = k\gamma^{n-1} e^{T0\ T} < \eta_{max}$ where k is a measure of the average viscosity of the fluid (index of consistency), n is a measure of the deviation from the Newtonian fluid (power law index), T0 is the reference temperature and $\eta_{min}$ and $\eta_{max}$ are respectively the lower and upper viscosity limits. The power law parameters utilised during the simulations are presented in Table 1 below.

TABLE 1

| | |
|---|---|
| Power law index (n) | 0.4851 |
| Consistency index k (kg·s^n-2/m) | 0.2073 |
| Reference temperature (° K.) | 310 |
| Upper viscosity limit $\eta_{max}$ (kg/m-s) | 0.00125 |
| Lower viscosity limit $\eta_{min}$ (kg/m-s) | 0.003 |

The capture device being preferably destined to be placed in a vein of the forearm, the vein model utilised was that of the basilic vein.

A basilic vein model has been developed on the basis of various anatomical studies including that by Baptista-Silva et al.

The basilic vein was modelled utilising the variables presented in Table 2 below (Munis, J. R., L. J. Bhatia S Fau-Lozada, and L. J. Lozada):

TABLE 2

| | |
|---|---|
| Diameter of the vein (mm) | 2.0 |
| Blood flow velocity (m · s–1) | 0.0720 |
| Peripheral venous pressure (mm Hg) | 13 |

The thrombogenicity was determined by the study of the shear stresses and the exposure time, with platelet activation appearing from a value of dyne·s/cm$^2$ referred to as the Hellums threshold (Bludszuweit, C.).

Results:
Determination of the optimal shape of the capture device:

Different shapes of capture device were tested. For each of these shapes, the influence of the capture device on the flow velocity, Reynolds number, shear stresses and platelet activation of the blood flow were determined. 3D mapping of the velocity vectors within and in the vicinity of the device was performed for different values of the blood flow velocity within the channel.

The different shapes tested are illustrated in FIGS. 7A to 7E. The results are summarised in Table 3.

TABLE 3

Figure 7A:
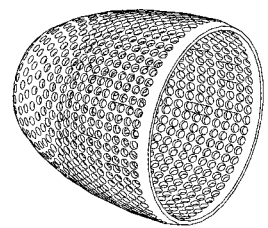
Figure 7B:
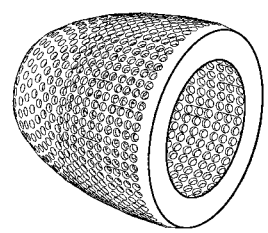
Figure 7C:
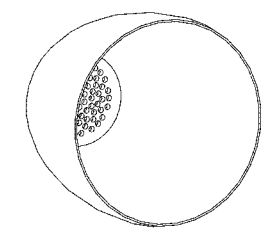
Figure 7D:
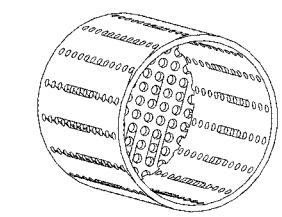
Figure 7E:
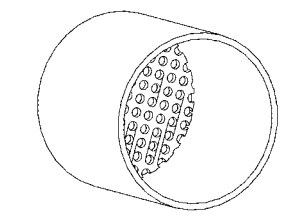

| Shape of the capture device | Results |
|---|---|
| FIG. 7A Shape of paraboloid type having apertures over the whole of the device | Conservation of the laminar nature of the blood flow (Re$_{max}$ = 28) Presence of two contra-rotating vortices in the interior of the capture device disappearing at velocities of 0.2 m/s Major decrease in the flow velocity in the interior of the capture device Absence of acceleration of the flow at the apertures Progressive increase in the pressure in the interior of the device (maximum value of 1400 Pa at the bottom of the device) Variation of the shear stresses between 9.43 and 36.3 Pa |
| FIG. 7B Shape of paraboloid type having apertures on the body of the device + full ring reducing the diameter of the central orifice | Conservation of the laminar nature of the blood flow Presence of two contra-rotating vortices at the bottom of the capture device (central reflux) |
| FIG. 7C Shape of paraboloid type with flat bottom having apertures only at the flat bottom | Conservation of the laminar nature of the blood flow Pressure conditions immediately maximal in the device Presence of two contra-rotating vortices of small size at the entrance of the capture device |
| FIG. 7D Shape of cylindrical type having apertures over the whole of the device | Conservation of the laminar nature of the blood flow Major decrease in the flow velocity in the interior of the capture device Absence of acceleration of the flow at the apertures Very progressive increase in the pressure in the interior of the device (maximum value of 1380 Pa at the bottom of the device) Presence of two contra-rotating vortices in the interior of the capture device |
| FIG. 7E Shape of cylindrical type having apertures only at the bottom of the cylinder | Conservation of the laminar nature of the blood flow Pressure immediately maximal at the entry of the device (maximum value of 1380 Pa in the interior of the device) Absence of contra-rotating vortices |

Conclusions

The paraboloid and cylindrical shapes make it possible to conserve the laminar nature of the blood flow.

The presence of contra-rotating vortices and hence the recirculation of the biomarkers is substantially decreased when the walls of the device are parallel to the flow and when the capture device has no apertures on its side walls.

Efficacy of Capture

Equipment and Methods

The conditions of circulation in a vein were reproduced in vitro.

The sample of blood tested is a sample of blood from a healthy volunteer sampled on Vacutainer® EDTA tubes (Becton, Dickinson & Company), to which PC3-GFP tumour cells were added at a concentration of 500 to 25000 tumour cells/ml.

Cylindrical capture devices such as that illustrated in FIG. 7B having different apertures were tested. These devices possess apertures with a diameter of 10 µm for the cylindrical apertures and 15 µm at entry and 8 µm at exit for the conical apertures. The viability of the captured cells was then evaluated by recovery of the cells by trypsinisation and reculturing of these in culture wells.

Results

TABLE 4

| Length | 6 µm | 150 µm | 150 µm | 150 µm | 150 µm |
|---|---|---|---|---|---|
| Wall thickness | 6 µm | 6 µm | 6 µm | 10 µm | 10 µm |
| Shape of apertures | cylindrical | cylindrical | conical | cylindrical | conical |
| Duration of experiment | 20 mins | 10 mins | 20 mins | 20 mins | 20 mins |
| Capture efficacy | − | +++ | + | ++ | + |

CONCLUSIONS

The results summarised in Table 4 show that the thickness and the length of the capture device have an influence on the capture efficacy. The capture device must have a given minimum length to allow the capture of cellular biomarkers. Without that minimum length the cellular biomarkers retained by the means of filtration are returned to circulation almost immediately in the biological flow. The thickness of the capture device also influences the capture efficacy. Too great a thickness can in fact decrease the capture efficacy.

The capture device allows the specific capture of cellular biomarkers such as CTCs. The other cells of the blood such as the leukocytes are not captured. Indeed, unlike CTCs, these latter have viscoelastic properties which allow them to pass through apertures smaller than their diameter.

The circular shape of the apertures is the most suitable for the capture of cellular biomarkers such as the CTCs. The diameter of the apertures must be adapted to the diameter of the biomarkers, but above all to the pressure conditions encountered in the peripheral venous system.

The captured cancer cells are viable after capture.

REFERENCES

Throughout this application, various references describe the prior art to which this invention belongs. The descriptions of these references are incorporated by reference into the present application.

Baptista-Silva, J. C. C, et al. Anatomy of the basilic vein in the arm and its importance for surgery, Braz J. Morphol. Sci., 2003, 20(3): p. 171-175

Bludszuweit, C., Three-dimensional numerical prediction of stress loading of blood particles in a centrifugal pump. (0160-564X (Print)).

Hellums, J., et al., Studies on the mechanisms of shear-induced platelet activation, in Cerebral ischemia and hemorheology. 1987, Springer. p. 80-89

Munis, J. R., L. J. Bhatia S Fau-Lozada, and L. J. Lozada, Peripheral venous pressure as a hemodynamic variable in neurosurgical patients. (0003-2999 (Print))

Nagrath, S., et al., Isolation of rare circulating tumour cells in cancer patients by microchip technology. Nature, 2007. 450 (7173): p. 1235-9

Petkova, S., et al. CFD modelling of bloodstream in portal vein hypertension with and without thrombosis. Third international conference on CFD in the minerals and process industries. 2003

Small, A. C., et al., The emerging role of circulating tumor cell detection in genitourinary cancer. J Urol, 2012. 188 (1): p. 21-6

Williams, A., et al. Clinical translation of a novel microfilter technology Capture, characterization and culture of circulating tumor cells. Point-of-Care Healthcare Technologies (PHT), 2013 IEEE.

The invention claimed is:

1. Device for sampling of cellular biomarkers circulating in an animal or human biological flow,
    wherein the cellular biomarkers are at least one of stromal and epithelial cells, circulating foetal cells (CFC), stem cells, clusters or aggregates of tumour cells, tumour cells, and monocytes (macrophages) and the device for sampling comprises at least one device for capture of cellular biomarkers attached onto a means of introduction of the at least one device for capture into a biological flow vessel,
    wherein the at least one device for capture is suitable for use in vivo and in that the at least one device for capture comprises a means of filtration intended to retain the cellular biomarkers, the means of filtration comprising at least one through-aperture the dimensions of which are suitable for retaining the cellular biomarkers and the means of filtration are planar and rigidly connected to a support, the support taking the form of a hollow component open at one end and closed at another end by the means of filtration and having a rotational symmetry about an axis which is total or truncated along a plane parallel to the axis enabling the at least one device for capture to conserve laminar nature of flow through the biological flow vessel upon introduction into the biological flow vessel, and
    wherein the means of filtration is configured to be inserted in a fully expanded configuration.

2. Device for sampling of cellular biomarkers according to claim 1, wherein the at least one through-aperture has at least one transverse dimension lying between 1 µm and 100 µm.

3. Device for sampling of cellular biomarkers according to claim 1, wherein the at least one through-aperture is substantially circular or substantially oval or substantially polygonal or takes the form of a crack.

4. Device for sampling of cellular biomarkers according to claim 1, wherein the at least one device for capture has a rotational symmetry about an axis.

5. Device for sampling of cellular biomarkers according to claim 1, wherein the support takes the form of a hollow cylinder, truncated along a plane parallel to the axis of the cylinder, the means of filtration closing one end of the truncated cylinder.

6. Device for sampling of cellular biomarkers according to claim 1, wherein the at least one device for capture is made of a photosensitive resin.

7. Device for sampling of cellular biomarkers according to claim 1, wherein the at least one device for capture is made of a biocompatible material or in that the at least one device for capture is covered with a biocompatible material.

8. Device for sampling of cellular biomarkers according to claim 1, wherein the at least one device for capture is functionalized by means of an anti-thrombotic compound.

9. Device for sampling of cellular biomarkers according to claim 1, wherein the means of introduction of the at least one device for capture into the blood circulation comprises a strip.

10. Device for sampling of cellular biomarkers according to claim 9, wherein the strip comprises a metallic alloy or a composite material based on resin and fibers.

11. Device for sampling of cellular biomarkers according to claim 1, wherein the means of introduction comprises a first means of protection of the means of filtration, intended to avoid detachment of the means of filtration.

12. Device for sampling of cellular biomarkers according to claim 11, wherein the first means of protection comprises at least one stud attached onto the means of introduction.

13. Device for sampling of cellular biomarkers according to claim 11, wherein the first means of protection is formed by an end piece attached to the extremity of the means of introduction.

14. Device for sampling of cellular biomarkers according to claim 13, wherein the end piece comprises at least one arch.

15. Device for sampling of cellular biomarkers according to claim 11, wherein the first means of protection is formed by at least one longitudinal arch which is contained by the means of introduction in the vicinity of its extremity.

16. Device for sampling of cellular biomarkers according to claim 11, wherein the means of introduction contains a second means of protection intended to protect a blood vessel into which the device for sampling is brought to be introduced and wherein the second, or the first and the second means of protection is formed by an end piece attached to the extremity of the means of introduction.

17. Device for sampling of cellular biomarkers according to claim 11, wherein the means of introduction contains a second means of protection intended to protect a blood vessel into which the device for sampling is brought to be introduced and wherein the second, or the first and the second means of protection is formed by at least one longitudinal arch which is contained by the means of introduction in the vicinity of its extremity.

18. Device for sampling of cellular biomarkers according to claim 1, wherein the means of introduction contains a second means of protection intended to protect a blood vessel into which the device for sampling is brought to be introduced.

19. Device for sampling of cellular biomarkers according to claim 1, wherein the device for sampling is covered with a biocompatible material.

20. Device for sampling of cellular biomarkers according to claim 1, wherein the device for sampling is functionalized by means of an anti-thrombotic compound.

21. Device for sampling of cellular biomarkers according to claim 1, wherein the device for sampling includes a means of gripping so as to render the device for sampling suitable for use in a catheter.

22. Set for sampling of cellular biomarkers comprising a catheter and a device for sampling according to claim 1, the device for sampling being inserted into the catheter.

23. Set for sampling of cellular biomarkers according to claim 22 for use for diagnostic or therapeutic purposes.

24. Device for sampling of cellular biomarkers according to claim 1 intended to be utilized for the diagnosis or therapy of cancer.

25. Device for sampling of cellular biomarkers according to claim 1 for use for diagnostic or therapeutic purposes.

26. Device for sampling of cellular biomarkers according to claim 1 for use for diagnostic or therapeutic purposes.

27. Device for sampling of cellular biomarkers according to claim 1, wherein the support is a cylinder, the wall of the cylinder is solid, and the cylinder is open at one end and closed at the other end by the means of filtration.

28. Device for sampling of cellular biomarkers circulating in an animal or human biological flow,
 wherein the cellular biomarkers are at least one of stromal and epithelial cells, circulating foetal cells (CFC), stem cells, clusters or aggregates of tumour cells, tumour cells, and monocytes (macrophages) and the device for sampling comprises at least one device for capture of cellular biomarkers attached onto a means of introduction of the at least one device for capture into a biological flow vessel,
 wherein the at least one device for capture is suitable for use in vivo and in that the at least one device for capture comprises a means of filtration intended to retain the cellular biomarkers, the means of filtration comprising at least one through-aperture the dimensions of which are suitable for retaining the cellular biomarkers and the means of filtration are planar and rigidly connected to a support, the support taking the form of a hollow component open at one end and closed at another end by the means of filtration and having a rotational symmetry about an axis which is total or truncated along a plane parallel to the axis,
 wherein the at least one device for capture is structured to enable flow through and around the at least one device for capture upon being inserted in the biological flow vessel.

* * * * *